US008422667B2

(12) United States Patent
Fitzgibbon et al.

(10) Patent No.: US 8,422,667 B2
(45) Date of Patent: Apr. 16, 2013

(54) METHOD AND APPARATUS TO FACILITATE TRANSMISSION OF AN ENCRYPTED ROLLING CODE (75) Inventors: James J. Fitzgibbon, Batavia, IL (US); Eric Gregori, Lindenhurst, IL (US)

(73) Assignee: The Chamberlain Group, Inc., Elmhurst, IL (US)

( * ) Notice: Subject to any disclaimer, the term of this patent is extended or adjusted under 35 U.S.C. 154(b) by 1560 days.

(21) Appl. No.: 11/501,455

(22) Filed: Aug. 9, 2006

(65) Prior Publication Data
US 2007/0058811 A1 Mar. 15, 2007

Related U.S. Application Data (63) Continuation-in-part of application No. 11/480,288, filed on Jun. 30, 2006, now Pat. No. 7,561,075, which is a continuation of application No. 11/044,411, filed on Jan. 27, 2005, now Pat. No. 7,071,850, said application No. 11/501,455 is a continuation-in-part of application No. 11/172,525, filed on Jun. 30, 2005.

(51) Int. Cl.
*H04K 1/00* (2006.01)
*H04L 9/00* (2006.01)
*H04L 9/28* (2006.01)

(52) U.S. Cl.
USPC ............................................. 380/28; 380/29

(58) Field of Classification Search ............ 380/28–30, 380/42–47
See application file for complete search history.

(56) References Cited

U.S. PATENT DOCUMENTS

| 3,906,348 A | 9/1975 | Willmott |
| 4,097,859 A | 6/1978 | Looschen |
| 4,178,549 A | 12/1979 | Ledenbach et al. |
| 4,243,976 A | 1/1981 | Warner et al. |
| 4,255,742 A | 3/1981 | Gable et al. |
| 4,387,455 A | 6/1983 | Schwartz |
| 4,387,460 A | 6/1983 | Boutmy et al. |
| 4,468,787 A | 8/1984 | Keiper, Jr. |
| 4,566,044 A | 1/1986 | Langdon, Jr. et al. |
| 4,677,284 A | 6/1987 | Genest |
| 4,750,118 A | 6/1988 | Heitschel et al. |
| 4,808,995 A | 2/1989 | Clark et al. |

(Continued)

FOREIGN PATENT DOCUMENTS

| EP | 1 223 700 | 7/2002 |
| EP | 1 313 260 A3 | 5/2003 |

(Continued)

OTHER PUBLICATIONS

Combined Search and Examination Report Under Sections 17 and 18(3) From British Application No. GB1000541.1 Dated Jan. 28, 2010.

(Continued)

*Primary Examiner* — Benjamin E Lanier
(74) *Attorney, Agent, or Firm* — Fitch Even Tabin & Flannery LLP (57) ABSTRACT An encrypted rolling code (11), a plurality of differing data bit order patterns (13), and a plurality of differing data inversion patterns 14 are provided. One then selects (15) a particular one of each of these patterns and uses those selected patterns as transmission characteristics when transmitting (16) at least part of the encrypted rolling code.

28 Claims, 9 Drawing Sheets

U.S. PATENT DOCUMENTS

| | | | |
|---|---|---|---|
| 4,829,296 | A | 5/1989 | Clark et al. |
| 4,893,338 | A | 1/1990 | Pastor |
| 4,910,750 | A | 3/1990 | Fisher |
| 4,988,992 | A | 1/1991 | Heitschel et al. |
| 5,021,776 | A | 6/1991 | Anderson et al. |
| 5,136,548 | A | 8/1992 | Claar et al. |
| 5,150,464 | A | 9/1992 | Sidhu et al. |
| 5,197,061 | A | 3/1993 | Halbert-Lassalle et al. |
| 5,252,960 | A | 10/1993 | Duhame |
| 5,420,925 | A | 5/1995 | Michaels |
| 5,442,340 | A | 8/1995 | Dykema |
| 5,517,187 | A | 5/1996 | Bruwer et al. |
| 5,565,812 | A * | 10/1996 | Soenen ............... 327/558 |
| 5,576,701 | A | 11/1996 | Heitschel et al. |
| 5,578,999 | A | 11/1996 | Matsuzawa et al. |
| 5,600,653 | A | 2/1997 | Chitre et al. |
| 5,635,913 | A | 6/1997 | Willmott et al. |
| 5,673,017 | A | 9/1997 | Dery et al. |
| 5,686,904 | A | 11/1997 | Bruwer |
| 5,699,065 | A | 12/1997 | Murray |
| 5,774,065 | A * | 6/1998 | Mabuchi et al. ......... 340/825.72 |
| 5,942,985 | A | 8/1999 | Chin |
| 5,949,349 | A | 9/1999 | Farris et al. |
| 6,012,144 | A | 1/2000 | Pickett |
| 6,049,289 | A | 4/2000 | Waggamon et al. |
| 6,052,408 | A | 4/2000 | Trompower et al. |
| 6,070,154 | A | 5/2000 | Tavor et al. |
| 6,154,544 | A * | 11/2000 | Farris et al. ............... 380/262 |
| 6,157,719 | A | 12/2000 | Wasilewski et al. |
| 6,175,312 | B1 | 1/2001 | Bruwer et al. |
| 6,181,255 | B1 | 1/2001 | Crimmins et al. |
| 6,414,587 | B1 | 7/2002 | Fitzgibbon |
| 6,456,726 | B1 | 9/2002 | Yu et al. |
| 6,496,477 | B1 | 12/2002 | Perkins et al. |
| 6,535,544 | B1 | 3/2003 | Partyka |
| 6,688,518 | B1 | 2/2004 | Valencia et al. |
| 6,690,796 | B1 | 2/2004 | Farris et al. |
| 6,697,379 | B1 | 2/2004 | Jacquet et al. |
| 6,754,266 | B2 | 6/2004 | Bahl et al. |
| 6,810,123 | B2 | 10/2004 | Farris et al. |
| 6,829,357 | B1 | 12/2004 | Alrabady et al. |
| 6,850,910 | B1 | 2/2005 | Yu et al. |
| 6,930,983 | B2 | 8/2005 | Perkins et al. |
| 6,963,561 | B1 | 11/2005 | Lahat |
| 6,980,518 | B1 | 12/2005 | Sun et al. |
| 6,980,655 | B2 | 12/2005 | Farris et al. |
| 6,998,977 | B2 | 2/2006 | Gregori et al. |
| 7,002,490 | B2 | 2/2006 | Lablans |
| 7,039,809 | B1 | 5/2006 | Wankmueller |
| 7,042,363 | B2 | 5/2006 | Katrak et al. |
| 7,050,479 | B1 | 5/2006 | Kim |
| 7,071,850 | B1 | 7/2006 | Fitzgibbon et al. |
| 7,139,398 | B2 | 11/2006 | Candelore et al. |
| 7,301,900 | B1 | 11/2007 | Laksono |
| 7,333,615 | B1 | 2/2008 | Jarboe et al. |
| 7,336,787 | B2 | 2/2008 | Unger et al. |
| 7,346,163 | B2 | 3/2008 | Pedlow et al. |
| 7,353,499 | B2 | 4/2008 | de Jong |
| 7,412,056 | B2 | 8/2008 | Farris et al. |
| 7,415,618 | B2 | 8/2008 | de Jong |
| 7,429,898 | B2 | 9/2008 | Akiyama et al. |
| 7,492,905 | B2 | 2/2009 | Fitzgibbon |
| 7,535,926 | B1 | 5/2009 | Deshpande et al. |
| 7,561,075 | B2 | 7/2009 | Fitzgibbon et al. |
| 7,623,663 | B2 | 11/2009 | Farris et al. |
| 7,668,125 | B2 | 2/2010 | Kadous |
| 7,786,843 | B2 | 8/2010 | Witkowski |
| 8,194,856 | B2 | 6/2012 | Farris et al. |
| 8,233,625 | B2 | 7/2012 | Farris et al. |
| 2001/0023483 | A1 | 9/2001 | Kiyomoto |
| 2002/0184504 | A1 | 12/2002 | Hughes |
| 2002/0191785 | A1 | 12/2002 | McBrearty et al. |
| 2002/0191794 | A1 | 12/2002 | Farris et al. |
| 2003/0056001 | A1 | 3/2003 | Mate et al. |
| 2003/0070092 | A1 | 4/2003 | Hawkes et al. |
| 2003/0072445 | A1 | 4/2003 | Kuhlman et al. |
| 2003/0147536 | A1 | 8/2003 | Andivahis et al. |
| 2003/0177237 | A1 | 9/2003 | Stebbings |
| 2004/0019783 | A1 | 1/2004 | Hawkes et al. |
| 2004/0081075 | A1 | 4/2004 | Tsukakoshi |
| 2004/0174856 | A1 | 9/2004 | Brouet et al. |
| 2004/0181569 | A1 | 9/2004 | Attar et al. |
| 2005/0053022 | A1 | 3/2005 | Zettwoch |
| 2005/0058153 | A1 | 3/2005 | Santhoff et al. |
| 2006/0109978 | A1 | 5/2006 | Farris et al. |
| 2006/0176171 | A1 | 8/2006 | Fitzgibbon et al. |
| 2007/0005806 | A1 | 1/2007 | Fitzgibbon et al. |
| 2007/0006319 | A1 | 1/2007 | Fitzgibbon et al. |
| 2007/0018861 | A1 | 1/2007 | Fitzgibbon et al. |
| 2008/0229400 | A1 | 9/2008 | Burke |
| 2008/0297370 | A1 | 12/2008 | Farris et al. |
| 2009/0016530 | A1 | 1/2009 | Farris et al. |
| 2009/0021348 | A1 | 1/2009 | Farris et al. |
| 2011/0316688 | A1 | 12/2011 | Ranjan et al. |
| 2011/0317835 | A1 | 12/2011 | Laird et al. |

FOREIGN PATENT DOCUMENTS

| | | |
|---|---|---|
| EP | 1760985 | 2/2007 |
| FR | 2737373 | 1/1997 |
| GB | 2288261 | 10/1995 |
| GB | 2430115 | 3/2007 |
| JP | 09322274 | 12/1997 |
| WO | WO 00/10301 | 2/2000 |

OTHER PUBLICATIONS

British Search Report for Application No. GB0613068.6 Dated Aug. 23, 2006.

British Examination Report Under Section 18(3) dated May 6, 2010 for British Application No. GB0613068.6.

Search Report Under Section 17; Application No. GB0715089.9: Date of Search: May 8, 2008.

Search Report Under Section 17; Application No. GB0601795.8; Date of Search: May 22, 2006.

Search Report Under Section 17; Application No. GB0613068.6; Date of Search: Aug. 23, 2006.

Australian Examiners First Report on Patent Application No. 2006202850 Dated Feb. 25, 2010.

British Examination Report Under Section 18(3); British Application No. GB0601795.8 Dated Apr. 22, 2009.

British Examination Report Under Section 18(3); British Application No. GB0601795.8 Dated Sep. 25, 2009.

British Examination Report Under Section 18(3); British Application No. GB0601795.8 Dated Jan. 28, 2010.

British Combined Search and Examination Report Under Sections 17 and 18(3); British Application No. GB0920612.9 Dated Dec. 16, 2009.

British Examination Report Under Section 18(3); British Application No. GB0613068.6 Dated Nov. 26, 2010.

British Examination Report Under Section 18(3); British Application No. GB0613068.6 Dated Jan. 31, 2011.

British Examination Report Under Section 17(5); British Application No. GB0715089.9 Dated Nov. 28, 2007.

British Examination Report Under Section 18(3); British Application No. GB0715089.9 Dated Sep. 30, 2010.

U.S. Office Action Dated Mar. 21, 2011 from U.S. Appl. No. 11/172,525.

British Examination Report Under Section 18(3); British Application No. GB0920612.9 Dated Jan. 28, 2010.

British Patent Application No. GB1110709.1; Combined Search and Examination Report Under Sections 17 and 18(3); Date of Search: Sep. 29, 2011.

British Patent Application No. GB1110710.9; Combined Search and Examination Report Under Sections 17 and 18(3); Date of Search: Sep. 30, 2011.

Examination Report Under Section 18(3) from British Patent Application No. GB0715089.9 dated Apr. 11, 2011.

Combined Search and Examination Report Under Sections 17 and 18(3) from British Patent Application No. GB1104752.9 dated Apr. 11, 2011.

Search Report Under Section 17 from British Patent Application No. GB0613068.6; Date of Search: Oct. 12, 2006.

U.S. Appl. No. 11/172,524; Office Action Dated Apr. 9, 2009.

* cited by examiner

| B7 | B6 | B5 | B4 | Order of bits | B3 | B2 | B1 | B0 | Inversion Pattern |
|----|----|----|----|---------------|----|----|----|----|-------------------|
| 0 | 0 | 0 | 0 | ABC | 0 | 0 | 0 | 0 | Normal Normal Normal |
| 0 | 0 | 0 | 1 | ACB | 0 | 0 | 0 | 1 | Normal Normal Invert |
| 0 | 0 | 1 | 0 | CBA | 0 | 0 | 1 | 0 | Normal Invert Normal |
| 0 | 1 | 0 | 0 | CAB | 0 | 1 | 0 | 0 | Normal Invert Invert |
| 0 | 1 | 0 | 1 | BAC | 0 | 1 | 0 | 1 | Invert Normal Normal |
| 0 | 1 | 1 | 0 | BCA | 0 | 1 | 1 | 0 | Invert Normal Invert |
| 1 | 0 | 0 | 0 | ACB | 1 | 0 | 0 | 0 | Invert Invert Normal |
| 1 | 0 | 0 | 1 | CAB | 1 | 0 | 0 | 1 | Invert Invert Invert |
| 1 | 0 | 1 | 0 | BCA | 1 | 0 | 1 | 0 | Invert Invert Invert |

METHOD AND APPARATUS TO FACILITATE TRANSMISSION OF AN ENCRYPTED ROLLING CODE

RELATED APPLICATIONS

This application is a continuation in part of application Ser. No. 11/480,288 which was filed on Jun. 30, 2006 as a continuation of application Ser. No. 11/044,411, which is entitled METHOD AND APPARATUS TO FACILITATE TRANSMISSION OF TERNARY MOVABLE BARRIER OPERATOR INFORMATION, which was filed on Jan. 27, 2005, and is now issued as U.S. Pat. No. 7,071,850; and This application is a continuation in part of application Ser. No. 11/172,525 filed Jun. 30, 2005 and entitled METHOD AND APPARATUS TO FACILITATE MESSAGE TRANSMISSION AND RECEPTION USING DIFFERENT TRANSMISSION CHARACTERISTICS the contents of which are fully incorporated herein by this reference.

TECHNICAL FIELD

This invention relates generally to encrypted rolling codes and more particularly to the transmission of encrypted rolling code information.

BACKGROUND

Rolling codes are known in the art. Rolling codes are often used, for example, in conjunction with movable barrier operators of various kinds (with movable barrier operators of various kinds also being known in the art and including operators that effect the selective control and movement of single panel and segmented garage doors, pivoting, rolling, and swinging gates, guard arms, rolling shutters, and various other movable barriers). In such an application setting, a wireless transmitter can send a code to a corresponding movable barrier operator to cause the latter to effect a desired movement or other action with respect to, for example, a corresponding movable barrier.

When using rolling codes, the code transmitted by the wireless transmitter will change (often with each transmission) in accordance with a predetermined plan or algorithm that is also known to the movable barrier operator. Such an approach can foil the use of an intercepted code by an unauthorized party because that intercepted code will not typically again, at least in the near term, be honored by that movable barrier operator should the unauthorized party attempt to themselves transmit that code. Without knowledge of the underlying scheme by which a next code is selected, the unauthorized party who gains access to a presently used code will still remain unable to leverage that knowledge in support of effecting unauthorized control over the movable barrier operator.

There may be instances, however, when additional security may be desired or appropriate. For example, a given rolling code instantiation may be open to brute force attacks or other weaknesses due to local and/or otherwise unique circumstances.

BRIEF DESCRIPTION OF THE DRAWINGS

The above needs are at least partially met through provision of the method and apparatus to facilitate transmission of an encrypted rolling code described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will also be understood that the terms and expressions used herein have the ordinary meaning as is accorded to such terms and expressions with respect to their corresponding respective areas of inquiry and study except where specific meanings have otherwise been set forth herein.

DETAILED DESCRIPTION

Generally speaking, pursuant to these various embodiments, an encrypted rolling code, a plurality of differing data bit order patterns, and a plurality of differing data inversion patterns are provided. One selects a particular one of each of the bit order patterns and the data inversion patterns to provide selected patterns and then uses those selected patterns as transmission characteristics when transmitting at least part of the encrypted rolling code.

By these teachings, for example, a wireless remote control transmitter can be provided with data to be transmitted, where that data comprises, at least in part, at least portions of an encrypted rolling code and where that data comports with a particular data bit order pattern and a particular data inversion pattern as a function of a given portion of that rolling code. That data can then be transmitted in combination with the given portion of the encrypted rolling code wherein that given portion of the rolling code is not transmitted with any of its bits reordered or inverted as a function of the given portion itself. Accordingly, a receiver that receives the data can then properly recover the re-ordered/inverted portions of the encrypted rolling code as a function of the given portion of the encrypted rolling code.

By one approach, if desired, the aforementioned data can comprise ternary data that is presented in a binary format. The use of ternary data can aid in facilitating compatible interaction with at least some movable barrier operators while also achieving an encryption effect at the same time as tending to ensure compatible use with binary peripheral platforms and the like. By one approach, this can comprise mapping each trit of the ternary data to a corresponding pair of binary bits. A pair of binary bits can represent 4 discrete information elements and by one approach, three of these discrete information elements can each correspond to one of the three trit states/levels while the fourth discrete information element (which otherwise comprises an illegal value) can serve a synchronization function.

If desired, in addition to the aforementioned encrypted rolling code, a fixed code can also be included in the transmission. By one approach, for example, both the aforementioned part of the encrypted rolling code and this fixed code can be transmitted using the above-described selected patterns as transmission characteristics.

Figure 1:
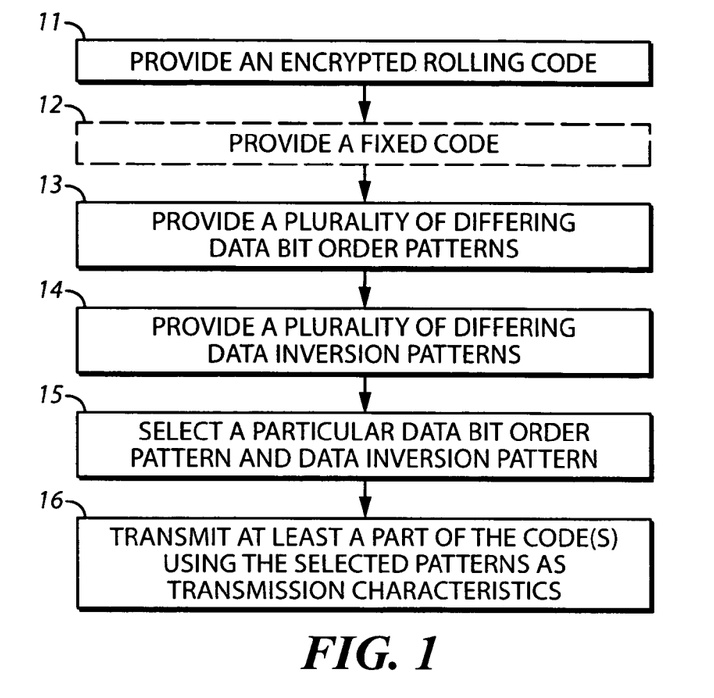
FIG. 1 comprises a flow diagram as configured in accordance with various embodiments of the invention.

These and other benefits may become clearer upon making a thorough review and study of the following detailed description. Referring now to the drawings, and in particular to FIG. 1, an illustrative process in this regard provides 11 an encrypted rolling code. As will be illustrated in more detail below, this can comprise, if desired, providing an encrypted rolling code as a plurality of bit pairs as correspond to a ternary data set.

If desired, this process will also optionally accommodate providing 12 a fixed code. This fixed code can vary with the needs, requirements, and/or opportunities of a given application setting, but can, for example, comprise a value that is substantially unique to a given transmitter and hence comprises a value that will serve to identify that given transmitter. Such an approach can be useful, for example, when used in conjunction with a remote control movable barrier operator transmitter.

This process also provides 13 a plurality of differing data bit order patterns. By one approach, for example, this can comprise data bit order patterns that each comprise a pattern for exactly three bits. As will be shown below, this can be particularly beneficial when used in conjunction with bit pairs that correlate to corresponding ternary data. Similarly, this process provides 14 a plurality of different data inversion patterns. As before, if desired, this can comprise providing patterns that each comprise a pattern for exactly three bits. The number of patterns provided in either case can vary as desired. By one approach, however, this can comprise providing at least nine different bit order patterns and nine different data inversion patterns. Illustrative examples in this regard are provided further herein.

This process then provides for selecting 15 a particular one of each of the data bit order patterns and the data inversion patterns to provide resultant corresponding selected patterns. There are various ways by which such selections can be made. By one approach, one may use a predetermined portion of the previously provided encrypted rolling code to inform the making of these selections. For example (and as will be illustrated in more detail herein), this can comprise using a predetermined four bit pairs of the encrypted rolling code as a basis for selecting the particular data bit order pattern and the particular data inversion pattern. As another example in this regard, in combination with the foregoing or in lieu thereof, this can comprise using a first predetermined portion of the encrypted rolling code to select a first particular data bit order pattern and a first data inversion pattern and using a second predetermined portion of the encrypted rolling code (that is, for example, discrete with respect to the first predetermined portion of the encrypted rolling code though this is not a fundamental requirement) to select a second particular data bit order pattern and a second data inversion pattern.

This process then provides for transmitting 16 at least a part of the encrypted rolling code itself (as well as at least a part of the above-described fixed code when present) using the aforementioned selected patterns as transmission characteristics. By one approach this can comprise making such a transmission using Manchester encoding as is known in the art.

So configured, these teachings are readily employed, for example, to facilitate the transmission of a remote control message. This can comprise, for example, providing a fixed message having at least a first part and a second part along with an encrypted rolling code that has a first through a fourth part. The first part of the encrypted rolling code can then be used to select a particular data bit order pattern and a data inversion pattern to use as a set of first selected patterns while the second part of the encrypted rolling code can be used to select a second set of patterns from amongst the available candidate patterns. One can then transmit the first part of the fixed message and the third part of the encrypted rolling code using the first selected patterns as transmission characteristics while transmitting the second part of the fixed message and the fourth art of the encrypted rolling code using the second selected patterns as transmission characteristics.

By one approach, in this illustrative example this can also comprise transmitting the first and second parts of the encrypted rolling code without using either the first or selected patterns as transmission characteristics. So configured, the first and second parts of the encrypted rolling code are then readily usable as recovery identifiers that can be used by a receiver to recover the first and second parts of the fixed message and the third and fourth parts of the encrypted rolling code.

To illustrate further in this regard, these first and second parts of the encrypted rolling code could each comprise four bit pairs as correspond to the aforementioned ternary data. In such a case, two of the bit pairs as comprise the first part of the encrypted rolling code can be used with a lookup table to correlate those two bit pairs to a corresponding data bit order pattern. In a similar manner the remaining bit pairs can be used with a second lookup table (which may, if desired, actually comprise a part of the first lookup table) to correlate these bit pairs with a corresponding data inversion pattern. In a similar fashion, two of the bit pairs of the four bit pairs as comprise the second part of the encrypted rolling code can be used with that first lookup table to identify another data bit order pattern while the remaining two bit pairs can be used with the second lookup table to identify a corresponding data inversion pattern.

In such a case, the aforementioned transmission can then comprise transmitting the second part of the fixed message and the fourth part of the encrypted rolling code using the second selected patterns as transmission characteristics only after not transmitting for at least a predetermined period of time following transmission of the first part of the fixed message and the third part of the encrypted rolling code using the first selected patterns as transmission characteristics. The duration of this predetermined period of time can vary with the needs and opportunities of a given application setting, but a duration of about 75 milliseconds will suffice for many expected purposes.

In addition to facilitating a transmission of an encrypted rolling code and other content that comprises, for example, information that is unique to a given transmitter (such as a unique identifier for that transmitter), these teachings will further readily accommodate the transmission of additional data that is not substantially unique to the transmitter. This can comprise, for example, providing a data payload (such as a remote control instruction such as OPEN, CLOSE, VACATION MODE, LIGHTS ON, LIGHTS OFF, and so forth) that is not substantially unique to a given transmitter and then transmitting the first part of the fixed message, the third part of the encrypted rolling code, and a first part of this data payload while using the first selected patterns as transmission characteristics and transmitting the second part of the fixed message, the fourth part of the encrypted rolling code, and a second (remaining) portion of the data payload using the second selected patterns as transmission characteristics. When the data payload comprises a relatively large quantity of data as compared to the fixed message and/or the encrypted rolling code, additional portions of the data payload as are not accommodated by the just-described process can then be supplementally transmitted using one of the already selected patterns (or other patterns, if desired) as transmission characteristics.

Figure 2:
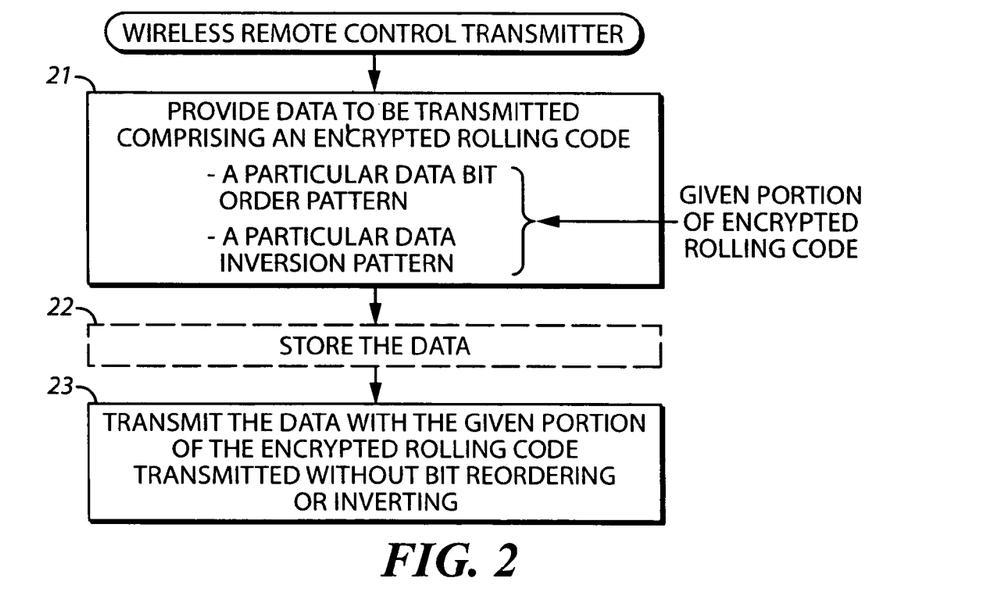
FIG. 2 comprises a flow diagram as configured in accordance with various embodiments of the invention.

As another specific illustrative example in this regard, and referring now to FIG. 2, a wireless remote control transmitter (such as a movable barrier operator remote control) can be configured and arranged to provide 21 data to be transmitted. This data can comprise, at least in part, at least portions of an encrypted rolling code. In any event, this data will comport with a particular data bit order pattern and a particular data inversion pattern as a function of a given portion of the rolling code. By one approach, if desired, this process can further comprise, at least in part, storing 22 this data in a memory prior to transmitting the data. The duration of such storage can vary considerably depending upon the specifics of a given application setting.

This wireless remote control transmitter can then transmit 23 this data in combination with the given portion of the encrypted rolling code such that the given portion of the encrypted rolling code is not transmitted with any of its bits reordered or inverted as a function of the given portion of the encrypted rolling code. So configured, a receiver that receives this data can properly recover the modified portions of the encrypted rolling code as a function, at least in part, of the unmodified given portion of the encrypted rolling code.

Figure 3:
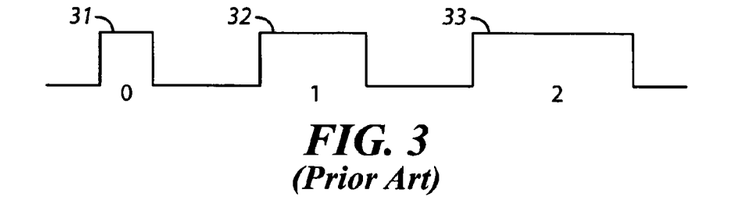
FIG. 3 comprises a depiction of prior art ternary encoding.

As noted above, these teachings are readily applied in a context that makes use of ternary data. It may therefore be helpful to first describe in more detail a typical ternary data protocol as one finds often deployed in conjunction with many movable barrier operators. Pursuant to one approach, pulses of similar amplitude have one of three different durations. For example, and referring now to FIG. 3, a first pulse 31, having a shortest duration, can represent the data element "0." A second pulse 32, having a medium length duration, can represent the data element or state "1." And a third pulse 33, having a longest duration, can represent the data element or state "2." Such a data mapping protocol serves well to effect a base three-based data exchange. The present teachings can accommodate use and leveraging of a ternary approach to effect relatively secure and compatible communications between a movable barrier operators and corresponding peripheral components of choice. These teachings are also compatible for use with an approach that eschews the specific ternary approach just described.

Figure 4:
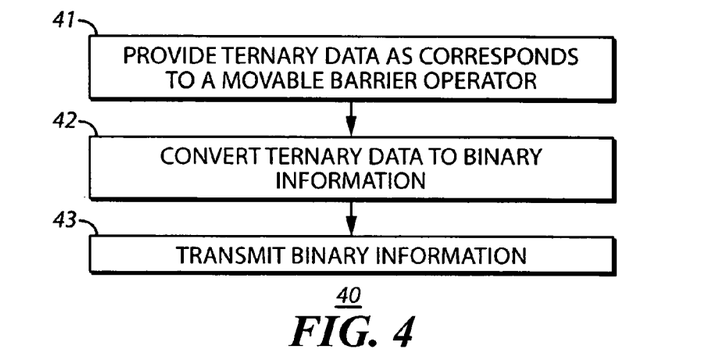
FIG. 4 comprises a flow diagram as configured in accordance with various embodiments of the invention.

Referring now to FIG. 4, in general, these teachings will accommodate a process 40 that itself provides 41 ternary data as corresponds to a movable barrier operator and then converts 42 that ternary data to a binary format to provide resultant binary information. This binary information is then transmitted 43 from one platform to another. As will be shown below, this ternary-to-binary conversion process serves, at least in part, as a kind of encryption process which in turn aids in ensuring the authenticity and accuracy of the information being transmitted.

Figure 5:
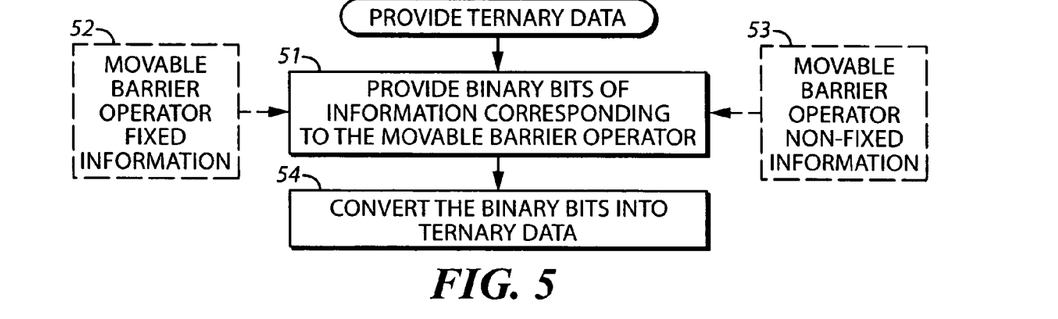
FIG. 5 comprises a flow diagram as configured in accordance with various embodiments of the invention.

The ternary data itself can comprise, at least in part, bearer data. More particularly, and referring momentarily to FIG. 5, pursuant to one (optional) approach, provision of ternary data can comprise prior provision 51 of binary bits comprising information that corresponds to the movable barrier operator (for example, information sourced by, or intended for, a movable barrier operator). Such information can optionally comprise, for example, movable barrier operator fixed information 52 such as identifying information for a particular movable barrier operator, a particular peripheral component, or the like. Such information can also optionally comprise (in addition to or in lieu of fixed information 52) non-fixed information 53 such as the aforementioned data payload as again corresponds to the movable barrier operator. This non-fixed information 53 can comprise bearer data/information (such as, but not limited to, platform status information, commands, acknowledgments, and so forth). As already noted, this non-fixed information 53 can also comprise varying quantities of data if desired.

These binary bits are then converted 54 into the aforementioned ternary data. This could comprise, in an appropriate platform, a conversion of the binary data into ternary data such as that described above with respect to FIG. 3. In general, such an approach need not be used. Instead, the binary data can be converted into a binary-bit-based ternary format (with an illustrative example being provided further below).

By one approach, however, this does not comprise a simple reversal of the binary-to-ternary process just described. Instead, the ternary-to-binary conversion step can comprise mapping each trit of the ternary data to a corresponding pair of binary bits. To illustrate such a map 61, and referring momentarily to FIG. 6, the ternary data element "0" (which corresponds to the usual binary data element "0") maps to the binary pair "00." In similar fashion, ternary "1" (which corresponds to usual binary "1") maps to the binary pair "01" and ternary "2" (which corresponds to usual binary "11") maps to the binary pair "01."

Figure 6:
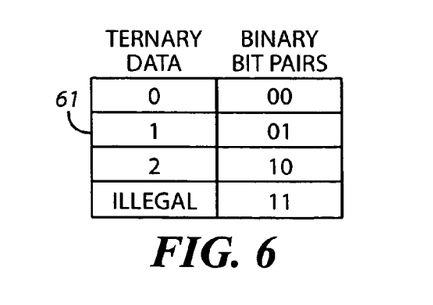
FIG. 6 comprises a mapping table as configured in accordance with various embodiments of the invention.

This leaves an otherwise unused binary pair "11." Pursuant to a preferred approach, this otherwise illegal value can serve a synchronization function when facilitating communications as between a movable barrier operator and one or more peripheral components when using a binary format that otherwise has no synchronization mechanism built into its format (for example, a stream of binary bits such as:

01101111111010011011011011111110100111011101101111111101001110111 which format lacks a frame marker or other point of synchronization). To illustrate, a synchronization signal/marker comprising this "11" binary pair can be used to indicate, for example, the regular end and/or start of a frame or message as in the following example:

110110111111011101101111011011111110111111011111110110111111111011111 where the bold font "11" regularly spaced binary pairs serve as frame markers (and which, due to their synchronized regular spacing, are readily distinguishable from other "11" pairs as may occur for whatever reason (illustratively depicted in the above example with italic font).

Those skilled in the art will appreciate that this process of converting binary information into ternary information, followed by conversion of that ternary information into corresponding binary pairs, yields, in most cases, a different bit sequence (and even a different number of bits) as compared to the initial binary information. This difference serves, at least in part, as a non-key-based encryption technique and hence provides a way of effecting the provision of an encrypted rolling code.

Figure 7:
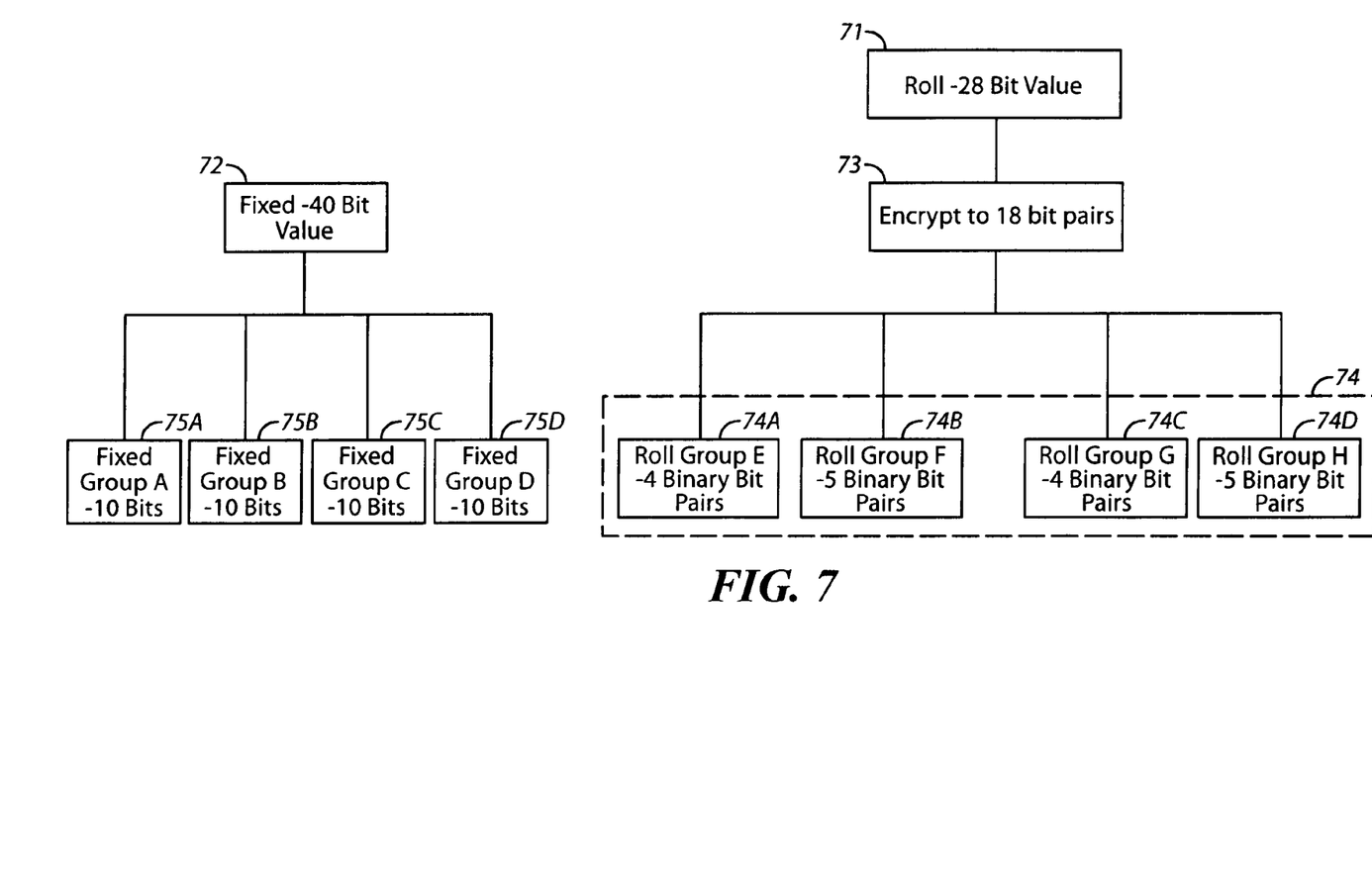
FIG. 7 comprises a schematic view of bit processing and parsing in accordance with various embodiments of the invention.

Referring now to FIG. 7, a more detailed illustrative embodiment will be presented. In this first illustrative example, the only substantive content to be associated and transmitted with a 28 bit rolling code 71 comprises a 40 bit value that represents fixed information 72. This fixed information 72 may serve, for example, to uniquely identify the transmitter that will ultimately transmit this information as noted above.

In this particular illustrative embodiment, the bits comprising the rolling code 71 are encrypted 73 by mirroring the bits and then translating those mirrored bits into ternary values as suggested above to provide corresponding bit pairs (in this example, this would comprise 18 such bit pairs) to thereby provide a resultant encrypted rolling code 74. This mirroring can be applied to specific groupings of bits in the rolling code creating mirrored groups or can involve the entire value. In this illustrative example, the encrypted rolling code 74 is presented for further processing as four groups. In this example, these four groups comprise a roll group E 74A comprised of four binary bit pairs, a roll group F 74B comprised of five binary bit pairs, a roll group G 74C comprised of four binary bit pairs, and a roll group H 74D comprised of five binary bit pairs.

The 40 bit fixed information 72 is subdivided in a similar manner albeit sans encryption. This comprises, in this particular illustrative approach, forming four subgroups comprising a fixed group A 75A, a fixed group B 75B, a fixed group C 75C, and a fixed group D 75D, wherein each such group is comprised of 10 bits of the original 40 bit value.

Figure 8:
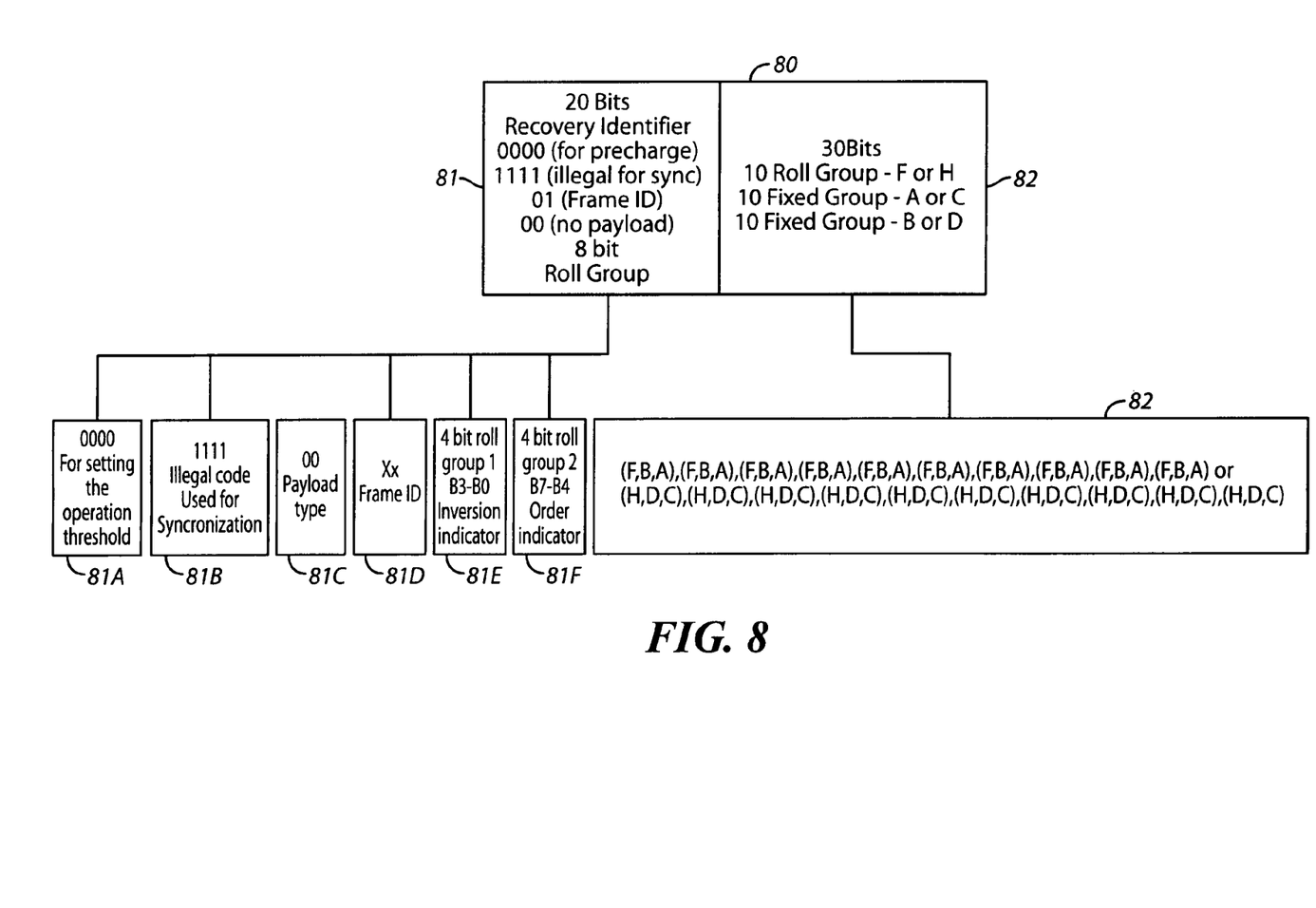
FIG. 8 comprises a comprises a schematic joint message diagram as configured in accordance with various embodiments of the invention.

These variously partitioned data groups can then be used as shown in FIG. 8 to effect a desired transmission. In this example, one or more joint messages 80 provide a primary vehicle by which to communicate the desired information (which includes both the encrypted rolling code and fixed information data as modified as a function of a given portion of the encrypted rolling code along with a recovery identifier that represents that given portion of the encrypted rolling code). This joint message 80 comprises, generally speaking, a first 20 bit portion 81 and a second 30 bit portion 82.

The first portion 81 comprises, in this embodiment, the following fields:
  "0000"—these bits 81A serve to precharge the decoding process and effectively establish an operational threshold;
  "1111"—these bits 81B comprise two bit pairs that present the illegal state "11" ("illegal" because this corresponds to a fourth unassigned state in the ternary context of these communications) and serve here as a basis for facilitating synchronization with a receiving platform;
  "00"—this bit pair 81C identifies a type of payload being borne by the joint message (in this embodiment, "00" corresponds to no payload other than the fixed identifying information for the transmitter itself, "01" corresponds to a supplemental data payload, and "10" corresponds to a supplemental data-only payload—further explanation regarding these payload types appears further below);
  "Xx"—this bit pair 81D presents a frame identifier that can be used by a receiver to determine whether all required joint messages 80 have been received and which can also be used to facilitate proper reconstruction of the transmitted data;
  "B3, B2, B1, B0"—these two bit pairs 81E comprise an inversion pattern recovery identifier and are selected from the bits that comprise the encrypted rolling code 74 described above;
  "B7, B6, B5, B4"—these two bit pairs 81F comprise a bit order pattern recovery identifier and are also selected from the bits that comprise the encrypted rolling code 74 described above.

Figure 9:
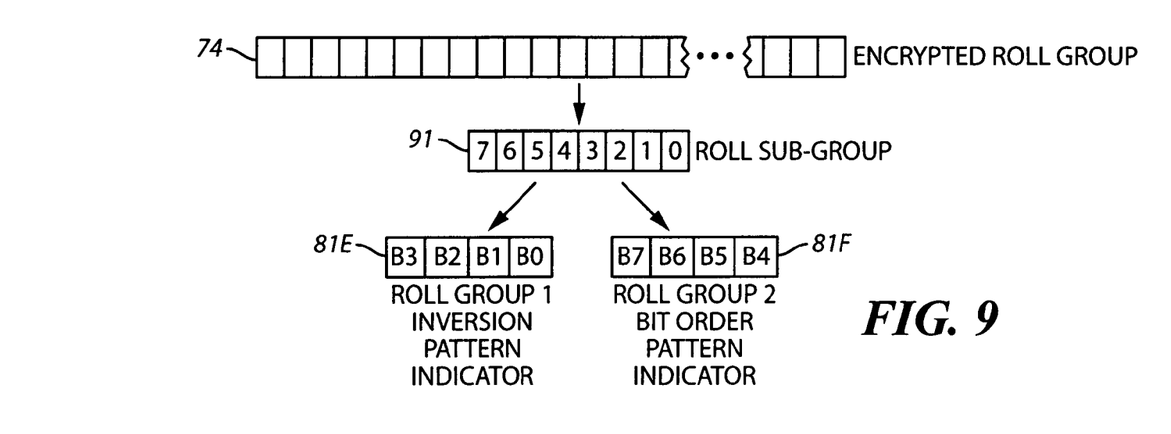
FIG. 9 comprises a schematic view of bit selection and parsing as configured in accordance with various embodiments of the invention.

There are various ways by which these recover identifier values can be selected. Referring momentarily to FIG. 9, by one approach, eight bits from the encrypted roll group 74 are selected to form a corresponding roll sub-group 91. These might comprise, for example, the first or the last eight bits of the encrypted roll group 74 (in a forward or reversed order). These might also comprise, for example, any eight consecutive bits beginning with any pre-selected bit position (such as, to illustrate, the seventh bit, the $21^{st}$ bit, and so forth). Other possibilities also exist. For example, only even position bits or odd position bits could serve in this regard. It would also be possible, for example, to use preselected bits as comprise one or more of the previously described roll group sub-groups such as roll group E 74A or roll group G 74C.

It would also be possible to vary the selection mechanism from, for example, joint message to joint message. By one simple approach in this regard, for example, the first eight bits of the encrypted roll group 74 could be used to form the roll sub-group 91 with the last eight bits of the encrypted roll group 74 being used in a similar fashion in an alternating manner.

The eight bits that comprise this roll sub-group 91 are then further parsed to form the two recovery indicators 81E and 81F mentioned above. Again, there are numerous ways by which one may use the bits that comprise the roll sub-group 91 to form these recovery indicators 81E and 81F. By one simple approach, for example, the bits as comprise the roll sub-group 91 can be used in their existing (or reversed) order to form roll group 1 81E and roll group 2 81F. Using this approach, for example, bit B3 of roll group 1 81E would comprise bit seven from the roll sub-group 91 with bit B2 then corresponding to bit six and so forth.

By another approach, if desired, every other bit can be applied in this manner. So configured, for example, bit B3 could comprise bit six from the roll sub-group 91, bit B2 could comprise bit four from the roll sub-group 91, and so forth. In such a case, bit B7 would then comprise bit seven from the roll sub-group 91, bit B6 would comprise bit five from the roll sub-group 91, and so forth.

Referring again to FIG. 8, in this embodiment, the "B7, B6, B5, B4" values from the corresponding recovery indicator are used in conjunction with one or more lookup tables to determine a data bit order pattern to use with respect to formatting the data as comprises the second portion 82 of the joint message 80. Similarly, the "B3, B2, B1, B0" values are used in conjunction with a lookup table to determine a data bit order pattern to also use with that second portion 82 of the joint message 80.

Before providing further elaboration regarding an illustrative example of such lookup tables and their use, it will be helpful to first note that, in this example, the data in the second portion 82 of the joint message comprises 10 bits from roll group F (or H) and 10 bits each from fixed group A (or C) and fixed group B (or D) for a total of 30 bits. These bits are organized into triplets (shown in FIG. 8 in the form "(F, B, A)" and "(H, D, C)" to indicate that each such triplet includes one bit from a roll group F or H and one bit each from the two fixed groups B and A or D and C.

Those skilled in the art will note that, in this illustrative example, bits from roll group E 74A and roll group G 74C are not present in the second portion 82 of the joint message 80. This is because, in this example, it is presumed that the contents of these two roll groups are used to form the recovery indicators that appear in the first portion 81 of the joint message 80. Other accommodations can of course be made in this regard. In general, however, these teachings will accommodate not including those encrypted rolling code bits that are used as recovery indicators in the second portion 82 of the joint message 80.

In the example shown, the order of the bits in each triplet is "F, B, A" (or "H, D, C" as appropriate). This order is neither arbitrary nor static. Instead, for this particular joint message 80, this order of the bits in each triplet is dictated by the values B7, B6, B5, B4 noted above. In this case, and referring now to FIG. 10, a lookup table 101 serves to correlate various values for these two bit pairs with corresponding data bit order patterns. In this example, presuming that the values of these four bits happens to be "0000," the corresponding order of bits for each triplet is established as "F/H, B/D, A/C" and hence the ordering of the bits depicted in FIG. 8.

Figure 10:
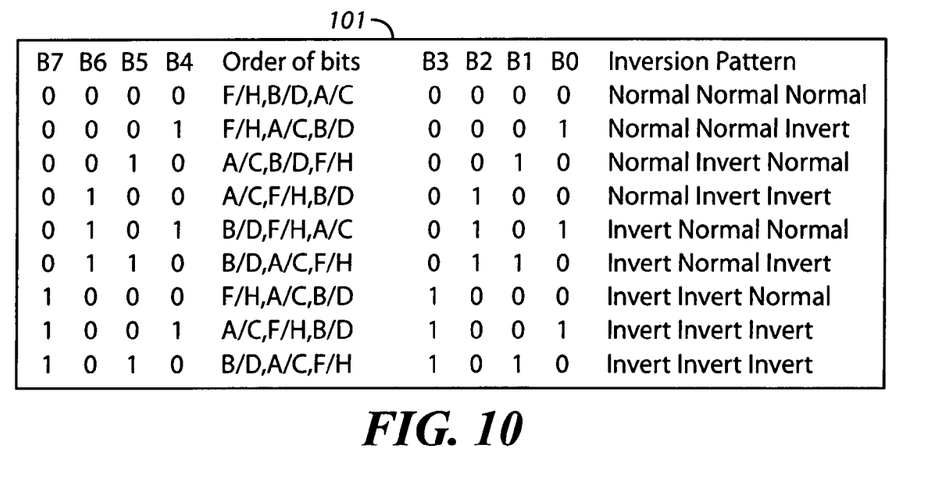
FIG. 10 comprises an illustrative example of a lookup table as configured in accordance with various embodiments of the invention.

Those skilled in the art will note that this lookup table 101 provides no patterns that would correlate to two bit pairs having the value "11." This is because, in this embodiment, "11" as a bit pair value comprises an illegal value and hence is not expected to occur. Accordingly there are no bit order patterns presented to correlate with such values as "11XX," "XX11," or "1111." This creates 9 possible selections for the order of bits and the inversion value. The number of possible unique order of three bits leads to only six different bit order patterns. This degree of diversity should suffice for most if not all purposes.

The aforementioned B3, B2, B1, B0 values 81F are employed in a similar fashion with this lookup table 101 to identify a particular inversion pattern to be employed with the data triplets of the second portion 82 of the joint message 80. For example, when these bits are "0000," this lookup table provides for no inversion of any of the bits in each triplet. On the other hand, when these bits are "1010," each bit of each triplet is to be inverted. In this case, up to eight different inversion patterns are possible.

To illustrate further, when a given data triplet happens to have the values "110" and the inversion indicator has the values "0100," the lookup table will return a data inversion pattern of "normal invert invert." As a result, this particular data triplet will instead have the values "101" because the second and third values in each triplet are now to be inverted in value.

So configured, a first portion of a joint message is seen to include a recovery indicator that itself comprises a selected portion of an encrypted rolling code. A second portion of that joint message, in turn, contains data triplets having bits that are arranged in a particular order and that observe a particular inversion pattern as a function of that joint indicator. Accordingly, it will not be sufficient for an unauthorized party to simply glean, in some fashion, the basis of the rolling code itself. Instead, now, this unauthorized party must also now understand how a particular portion of that rolling code is used to modify the transmission of other portions of that rolling code in addition to fixed information as may also accompany the rolling code.

In many application settings it may be desirable to present more than one such joint message to present a complete transmission. For example, and referring now to FIG. 11, it may be desirable to use two (or more) such joint messages 80A and 80B in order to present the complete rolling code and the complete fixed content and was described above. In such a case, for example, the first joint message 80A can present and use a first roll sub-group 91 as defined above as a recovery identifier (which comprises, in this illustrative example, roll group E 74A) while the second joint message 80B presents and uses a second, different roll sub-group B 91 (which comprises, in this illustrative example, roll group G 74C) for this purpose. These recovery identifiers can be used as just described to control modification of their corresponding data. So configured, in this illustrative example, 10 bits of roll group F 74B, 10 bits of fixed group A 75A, and 10 bits of fixed group B 75B have their bits ordered and inverted as a function of the bits of roll group E 74A while 10 bits of roll group H 74D, 10 bits of fixed group C 75C, and 10 bits of fixed group D 75D are similarly ordered/inverted as a function of the bits of roll group G 74C.

Figure 11:
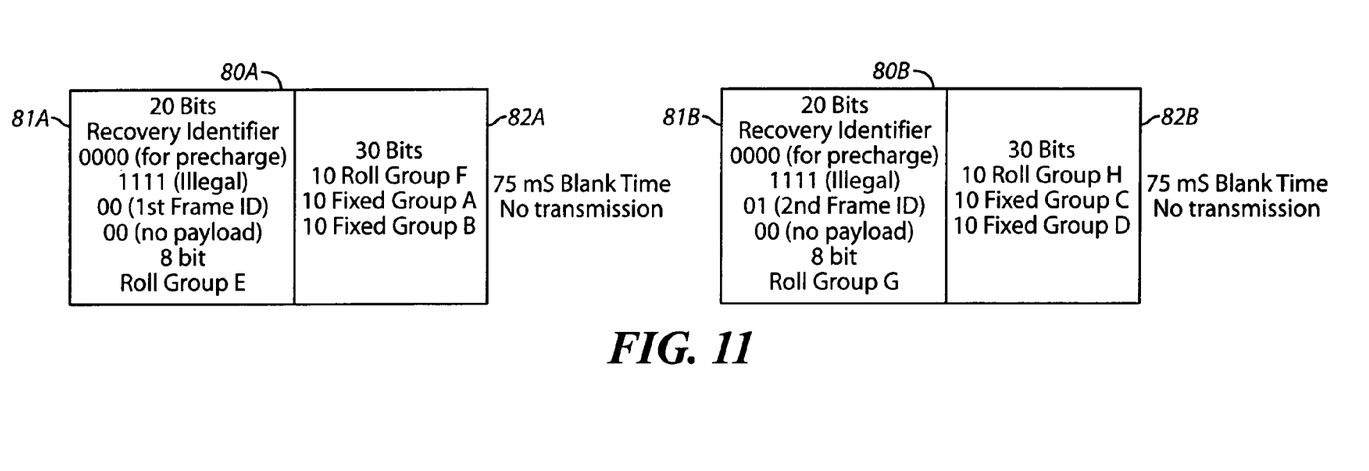
FIG. 11 comprises a schematic view of two joint messages as configured in accordance with various embodiments of the invention.

If desired, these joint messages 80A and 80B can be sent in a concatenated manner. By another approach, however, these joint messages can be separated by at least a minimal amount of silence (achieved, for example, by not transmitting during this period of time). For example, 75 milliseconds or so of blank time can be used for this purpose. So configured, a receiver that receives a second joint message prior to this period of blank time expiring can conclude that one or both of the received messages is somehow in error and should be avoided.

Figure 12:
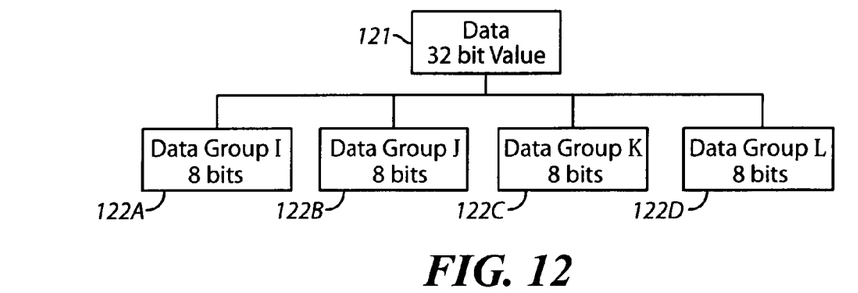
FIG. 12 comprises a schematic view of bit parsing as configured in accordance with various embodiments of the invention.

As noted above, in some cases it may be useful to transmit an additional amount of data or information than that specifically provided above. For example, it may be useful to transmit additional data that represents a particular instruction, status information, or the like. Such additional information can be readily accommodated by the teachings set forth above. To illustrate, and referring now to FIG. 12, 32 bits of such additional data can be subdivided into four corresponding data groups I and J 122A and 122B and K and L 122C and 122D where each such data group has eight bits.

Figure 13:
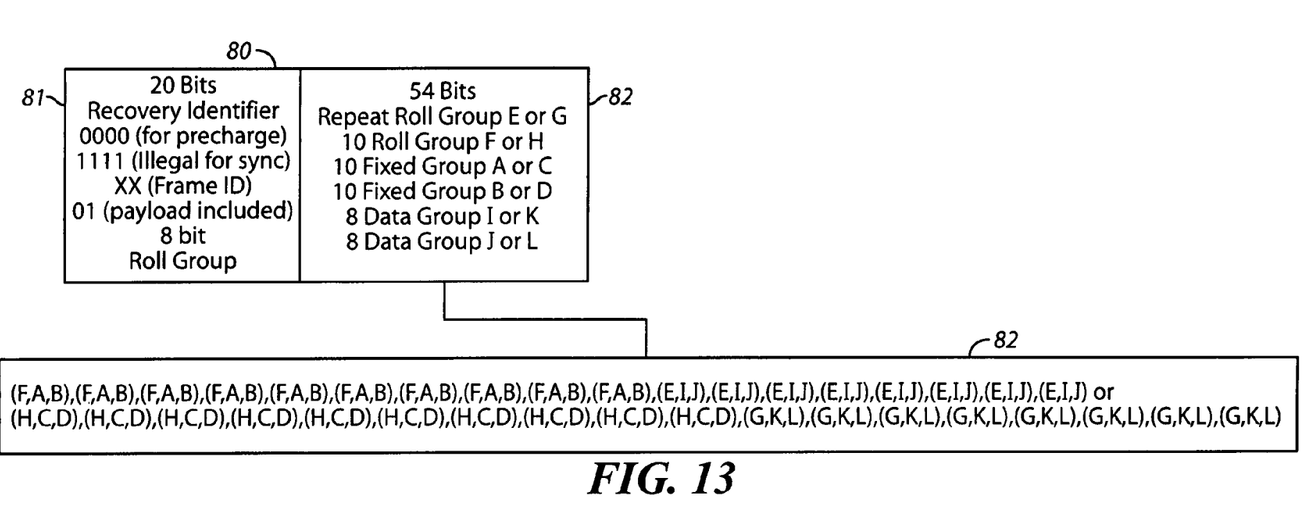
FIG. 13 comprises a schematic view of a joint message as configured in accordance with various embodiments of the invention.
Figure 14:
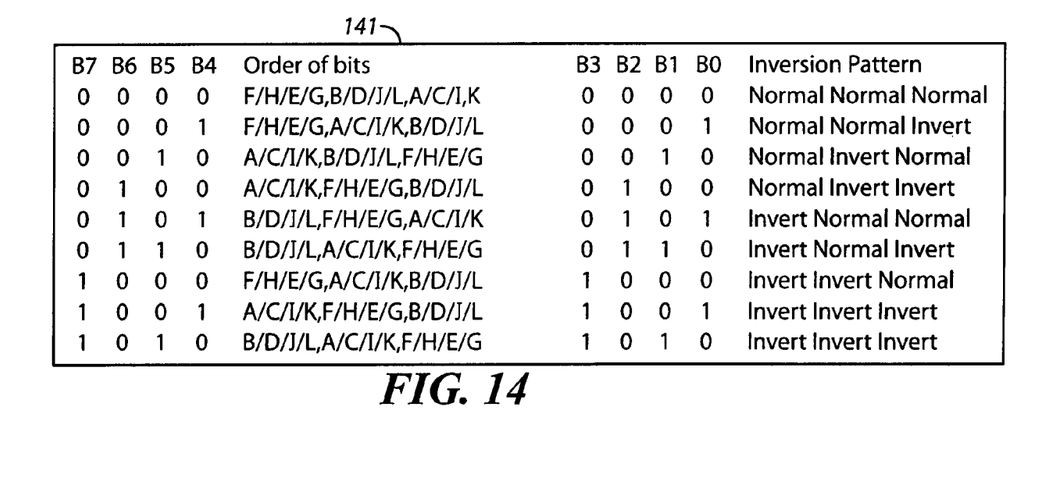
FIG. 14 comprises an illustrative example of a lookup table as configured in accordance with various embodiments of the invention.

Referring now to FIG. 13, the second portion 82 of each joint message 80 can now comprise 54 bits. By one approach, this can comprise 8 bits for a repeated presentation of the same rolling code group E or G as comprises the recovery identifier, 10 bits each for rolling code group F or H, fixed group A or C, and fixed group B or D, as well as 8 bits each for data group I or K and data group J or L as are described above. These various bits are again combined into data triplets using a group selection pattern such as that illustrated in FIG. 13. And, once again, the recovery identifier comprised of the roll group presented in the first portion 81 of the joint message 80 is used to select from a lookup table(s) the particular bit order and inversion patterns to employ with respect to these data triplets. In this case, and referring now to FIG. 14, the lookup table 141 can include specific bit order patterns that apply in different ways depending upon whether the data triplet includes the supplemental data.

Figure 15:
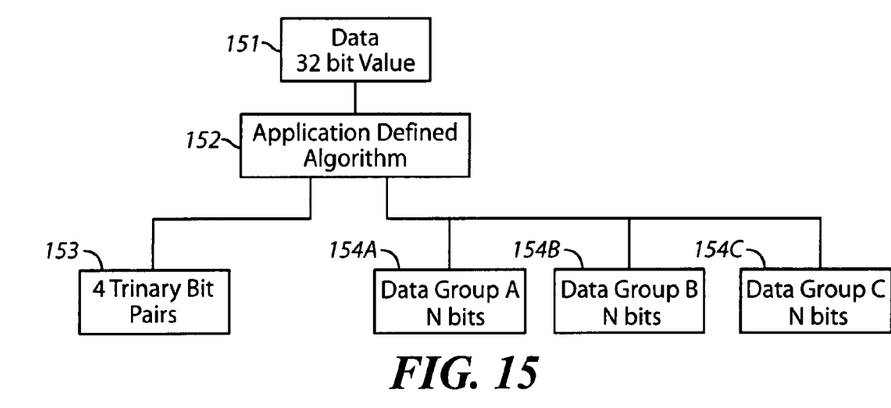
FIG. 15 comprises a schematic view of bit processing and parsing as configured in accordance with various embodiments of the invention.

In some cases, it may be necessary or appropriate to transmit even a larger quantity of data than can be accommodated by the processes and techniques described above. In such a case, if desired, additional supplemental joint messages can be used to present such supplemental data. With reference to FIG. 15, 32 bit value data elements 151 can be parsed using an application defined algorithm 152 of choice as corresponds to the data itself (or as may be otherwise provided or selected) into four ternary bit pairs 153 and three data groups of N bits each 154A-154C.

Figure 16:
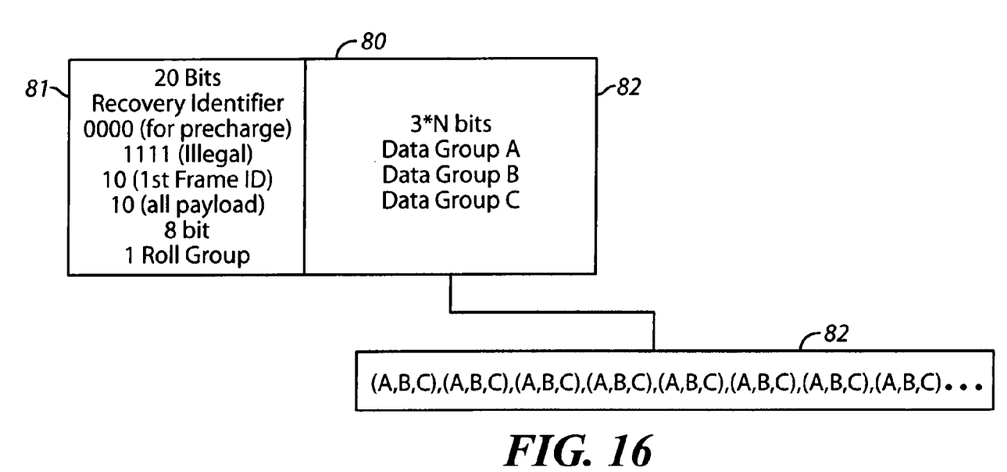
FIG. 16 comprises a schematic view of a joint message as configured in accordance with various embodiments of the invention.
Figure 17:
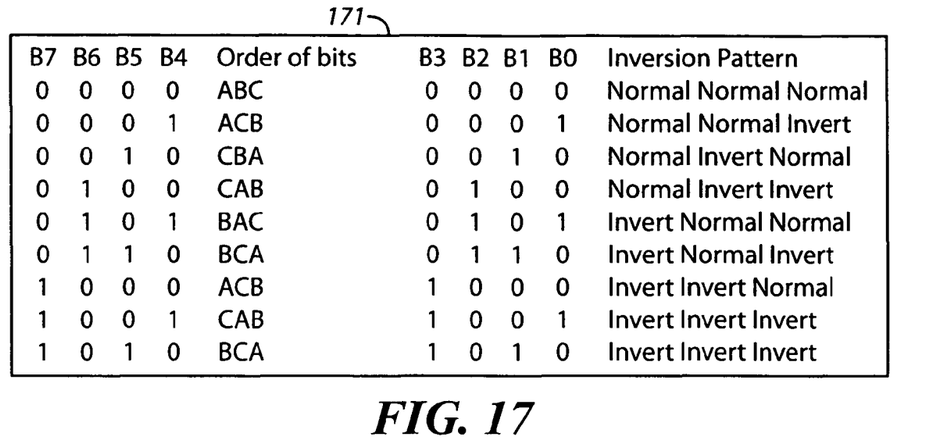
FIG. 17 comprises an illustrative example of a lookup table as configured in accordance with various embodiments of the invention.

Referring now to FIG. 16, the recovery indicator can be reused from a previous related joint message and the second portion 82 of the joint message 80 can contain 3 to the Nth power bits as necessary to accommodate the full data payload. The three data groups A-C are then used to form corresponding data triplets. And, as before, the recovery identifier is used to extract from a corresponding lookup table (such as the lookup table 171 presented in FIG. 17) the particular bit order pattern and bit inversion pattern to employ with respect to the transmission of these data triplets.

Figure 18:
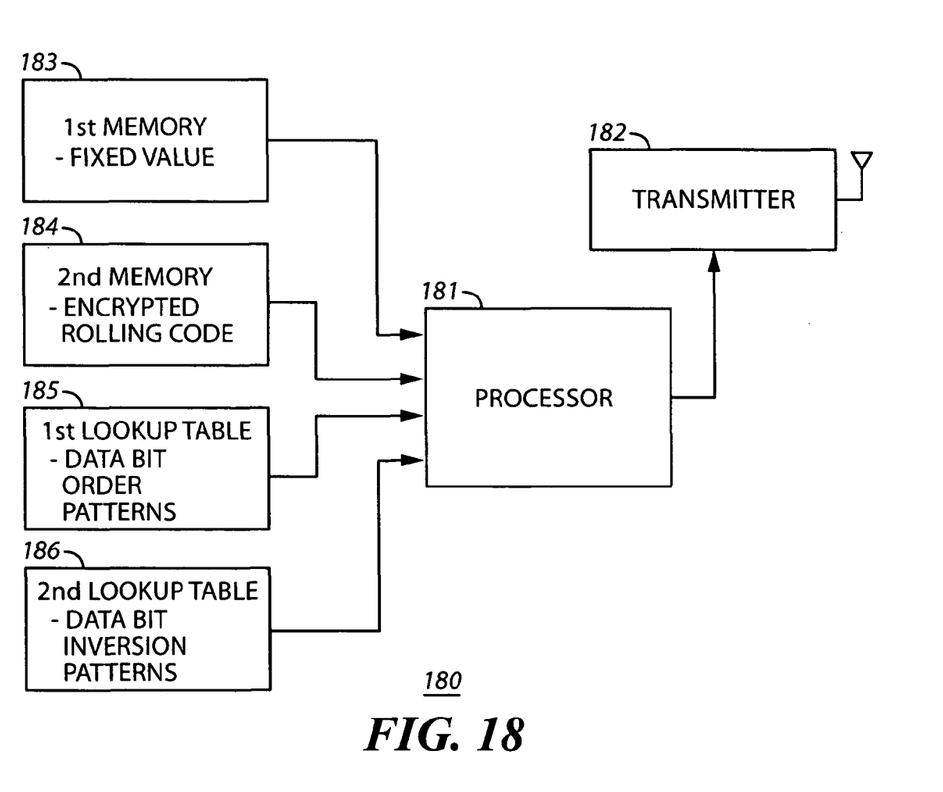
FIG. 18 comprises a block diagram as configured in accordance with various embodiments of the invention.

Those skilled in the art will appreciate that the above-described processes are readily enabled using any of a wide variety of available and/or readily configured platforms, including partially or wholly programmable platforms as are known in the art or dedicated purpose platforms as may be desired for some applications. Referring now to FIG. 18, an illustrative approach to such a platform will now be provided.

In this illustrative embodiment, the apparatus 180 (which may comprise, for example, a wireless remote control transmitter) comprises a processor 181 that couples to a transmitter 182 (such as a wireless transmitter) of choice. Both of these components then also operably couple to a first memory 183, a second memory 184, a first lookup table 185, and a second lookup table 186. The first memory 183 can have a fixed value stored therein. This fixed value can comprise, for example, information that substantially uniquely identifies this particular apparatus 180. This first memory 183 may also, if desired, have a plurality of different fixed values contained therein. This would permit storing, for example, remote control signals that are not specific (i.e., unique) to the apparatus 180 itself.

The second memory 184 can have the aforementioned encrypted rolling code stored therein. By one approach, the processor 181 is configured and arranged to calculate the encrypted rolling code when needed and to temporarily buffer that value in the second memory 184 pending actual use of that information. By another approach, the encrypted rolling code information can be pre-provisioned using a derivation and storage approach of choice.

The lookup tables 185 and 186 are the lookup tables described above. For example, the first lookup table 185 can comprise the lookup table that correlates a first plurality of different encrypted rolling code values with corresponding differing data bit order patterns. Similarly, the second lookup table 186 can comprise the lookup table that correlates a second plurality of different encrypted rolling code values with corresponding different data inversion patterns.

The processor 181 itself is configured and arranged (via, for example, appropriate programming) to carry out selected teachings as have been presented above. So configured, for example, the processor 181 can be configured and arranged to use the encrypted rolling code to select ones of the particular data bit order patterns and data inversion patterns for the transmitter 182 to use as transmission characteristics when transmitting the fixed value and at least portions of the encrypted rolling code. In particular, if desired, the processor can use a first part of the encrypted rolling code to select a data bit order pattern and a data inversion pattern to use when transmitting a first part of the encrypted rolling code and the fixed value and a second, different part of the encrypted rolling code to select a data bit order pattern and a data inversion pattern to use when transmitting a second, different part of the encrypted rolling code and the fixed value.

Those skilled in the art will recognize and understand that such an apparatus 180 may be comprised of a plurality of physically distinct elements as is suggested by the illustration shown in FIG. 18. It is also possible, however, to view this illustration as comprising a logical view, in which case one or more of these elements can be enabled and realized via a shared platform and/or a more-widely-distributed platform. It will also be understood that such a shared platform may comprise a wholly or at least partially programmable platform as are known in the art.

So configured, those skilled in the art will recognize and appreciate that these teachings offer great flexibility and opportunity with respect to further protecting information during a wireless transmission of that information. These teachings have particular relevance to transmissions of rolling codes and offer particular advantages when also used in conjunction with the transmission of fixed information in addition to rolling code information. The particular transmission characteristics presented are largely compatible for use with a wide variety of wireless modulation techniques. Those skilled in the art will also appreciate that these teachings are highly compatible for use with binary-based representations of ternary data formats.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method comprising:
providing an encrypted rolling code;
providing a plurality of differing data bit order patterns;
providing a plurality of differing data inversion patterns;
selecting a particular one of each of the data bit order patterns and the data inversion patterns to provide selected patterns;
transmitting at least a part of the encrypted rolling code using the selected patterns as transmission characteristics,
wherein selecting a particular one of each of the data bit order patterns and the data inversion patterns to provide selected patterns comprises using the rolling code to select the particular data bit order pattern and data inversion pattern to provide the selected patterns.

2. The method of claim 1 wherein the encrypted rolling code comprises a plurality of bit pairs.

3. The method of claim 1 wherein the differing data bit order patterns each comprise a pattern for exactly three bits.

4. The method of claim 1 wherein the differing data inversion patterns each comprise a pattern for exactly three bits.

5. The method of claim 1 wherein:
providing a plurality of differing data bit order patterns comprises providing at least six different bit order patterns; and providing a plurality of differing data inversion patterns comprises providing at least eight different data inversion patterns.

6. The method of claim 1 wherein using the encrypted rolling code to select the particular data bit order pattern and data inversion pattern to provide the selected patterns comprises using a predetermined portion of the encrypted rolling code to select the particular data bit order pattern and data inversion pattern to provide the selected patterns.

7. The method of claim 6 wherein using a predetermined portion of the encrypted rolling code to select the particular data bit order pattern and data inversion pattern to provide the selected patterns comprises using a predetermined four bit pairs of the encrypted rolling code to select the particular data bit order pattern and data inversion pattern to provide the selected patterns.

8. The method of claim 6 wherein using a predetermined portion of the encrypted rolling code to select the particular data bit order pattern and data inversion pattern to provide the selected patterns further comprises:
using a first predetermined portion of the encrypted rolling code to select a first particular data bit order pattern and a first data inversion pattern to provide first selected patterns; and
using a second predetermined portion of the encrypted rolling code to select a second particular data bit order pattern and a second data inversion pattern to provide second selected patterns;
wherein the first and second predetermined portions of the encrypted rolling code are discrete from one another.

9. The method of claim 1 further comprising:
providing a fixed code;
and wherein transmitting at least a part of the encrypted rolling code using the selected patterns as transmission characteristics further comprises transmitting at least a part of the encrypted rolling code and the fixed code using the selected patterns as transmission characteristics.

10. A method to facilitate transmitting a remote control message comprising:
providing a fixed message having at least a first and second part;
providing an encrypted rolling code having at least a first, second, third, and fourth part;
providing a plurality of differing data bit order patterns;
providing a plurality of differing data inversion patterns;
using the first part of the encrypted rolling code to select a particular one of each of the data bit order patterns and the data inversion patterns to provide first selected patterns;
using the second part of the encrypted rolling code to select a particular one of each of the data bit order patterns and the data inversion patterns to provide second selected patterns;
transmitting:
the first part of the fixed message and the third part of the encrypted rolling code using the first selected patterns as transmission characteristics; the second part of the fixed message and the fourth part of the encrypted rolling code using the second selected patterns as transmission characteristics.

11. The method of claim 10 wherein transmitting further comprises:
transmitting the first and second parts of the encrypted rolling code without using either the first or second selected patterns as transmission characteristics to thereby provide recovery identifiers to be used when recovering at a receiver the first and second parts of the fixed message and the third and fourth parts of the encrypted rolling code.

12. The method of claim 11 wherein the first and second parts of the encrypted rolling code each comprise four bit pairs.

13. The method of claim 12 wherein
using the first part of the encrypted rolling code to select a particular one of each of the data bit order patterns and the data inversion patterns to provide first selected patterns comprises using two bit pairs of the four bit pairs as comprise the first part of the encrypted rolling code and a first lookup table to correlate the two bit pairs to a corresponding data bit order pattern and using a different two bit pairs of the four bit pairs as comprise the first part of the encrypted rolling code and a second lookup table to correlate the different two bit pairs to a corresponding data inversion pattern;
using the second part of the encrypted rolling code to select a particular one of each of the data bit order patterns and the data inversion patterns to provide second selected patterns comprises using two bit pairs of the four bit pairs as comprise the second part of the encrypted rolling code and the first lookup table to correlate the two bit pairs to a corresponding data bit order pattern and using a different two bit pairs of the four bit pairs as comprise the second part of the encrypted rolling code and the second lookup table to correlate the different two bit pairs to a corresponding data inversion pattern.

14. The method of claim 13 wherein transmitting comprises transmitting using Manchester encoding.

15. The method of claim 14 wherein transmitting further comprises:
transmitting the second part of the fixed message and the fourth part of the encrypted rolling code using the second selected patterns as transmission characteristics only after not transmitting for at least a predetermined period of time following transmission of the first part of the fixed message and the third part of the encrypted rolling code using the first selected patterns as transmission characteristics.

16. The method of claim 15 wherein the predetermined period of time comprises about 75 milliseconds.

17. The method of claim 10 wherein the fixed message comprises a value that is substantially unique to a given transmitter and therefore serves to identify the given transmitter.

18. The method of claim 17 further comprising:
providing a data payload that is not substantially unique to the given transmitter; and wherein transmitting:
the first part of the fixed message and the third part of the encrypted rolling code using the first selected patterns as transmission characteristics;
the second part of the fixed message and the fourth part of the encrypted rolling code using the second selected patterns as transmission characteristics; further comprises:
transmitting:
the first part of the fixed message, the third part of the encrypted rolling code, and a first part of the data payload using the first selected patterns as transmission characteristics;
the second part of the fixed message, the fourth part of the encrypted rolling code, and a second part of the data payload using the second selected patterns as transmission characteristics.

19. The method of claim 18 wherein the data payload comprises a movable barrier operator remote control signal.

20. The method of claim 19 wherein transmitting further comprises transmitting a remaining part of the data payload using one of the selected patterns as transmission characteristics.

21. An apparatus comprising:
a first memory having a fixed value stored therein;
a second memory having an encrypted rolling code stored therein;
a first lookup table that correlates a first plurality of different encrypted rolling code values with corresponding differing data bit order patterns;
a second lookup table that correlates a second plurality of different encrypted rolling code values with corresponding differing data inversion patterns;
a processor that is operably coupled to the first and second memory and the first and second lookup table and that is configured and arranged to use the encrypted rolling code to select ones of the particular data bit order patterns and data inversion patterns to provide selected patterns;
a transmitter operably coupled to the first and second memory and to the processor and being configured and arranged to transmit at least a part of the encrypted rolling code and the fixed value using the selected patterns as transmission characteristics.

22. The apparatus of claim 21 wherein the apparatus comprises a movable barrier operator wireless remote control.

23. The apparatus of claim 21 wherein the processor is further configured and arranged to use:
a first part of the encrypted rolling code to select a data bit order pattern and a data inversion pattern to use when transmitting a first part of the encrypted rolling code and the fixed value; and
a second, different part of the encrypted rolling code to select a data bit order pattern and a data inversion pattern to use when transmitting a second, different part of the encrypted rolling code and the fixed value.

24. The apparatus of claim 21 wherein the fixed value comprises at least one of:
a substantially unique identifier for the apparatus;
a remote control signal that is not specific to the apparatus.

25. The apparatus of claim 24 wherein the fixed value comprises both of the substantially unique identifier for the apparatus and the remote control signal that is not specific to the apparatus.

26. A method for use with a receiver that is configured and arranged to compatibly receive and process a transmitted encrypted rolling code, wherein:
the transmitted encrypted rolling code comprises at least a part thereof that was transmitted using selected patterns of transmission characteristics selected based at least in part on a rolling code, wherein a first one of the selected patterns comprises a selected particular one of a plurality of differing data bit order patterns and wherein a second one of the selected patterns comprises a selected particular one of a plurality of differing data inversion patterns;
the method comprising:
at a transmitter:
providing a message that will be compatibly received and processed by the receiver as the transmitted encrypted rolling code;
transmitting the message to the receiver.

27. The method of claim 26 wherein providing a message comprises providing a message that comprises, at least in part, a representation of the selected patterns of transmission characteristics.

28. The method of claim 26 wherein transmitting the message to the receiver comprises transmitting the message to the receiver via a wireless connection.

* * * * *

UNITED STATES PATENT AND TRADEMARK OFFICE
CERTIFICATE OF CORRECTION

| | | |
|---|---|---|
| PATENT NO. | : 8,422,667 B2 | Page 1 of 1 |
| APPLICATION NO. | : 11/501455 | |
| DATED | : April 16, 2013 | |
| INVENTOR(S) | : James J. Fitzgibbon et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1401 days.

Signed and Sealed this
Eleventh Day of November, 2014

Michelle K. Lee
*Deputy Director of the United States Patent and Trademark Office*